US006969523B1

(12) United States Patent
Mattern et al.

(10) Patent No.: US 6,969,523 B1
(45) Date of Patent: Nov. 29, 2005

(54) COLLAGEN/GLYCOSAMINOGLYCAN MATRIX STABLE TO STERILIZING BY ELECTRON BEAM RADIATION

(75) Inventors: Ralph-Heiko Mattern, San Diego, CA (US); Michael D. Pierschbacher, San Diego, CA (US); Fred Cahn, La Jolla, CA (US); Juerg Friederich Tschopp, San Diego, CA (US); Timothy Irvin Malaney, Chula Vista, CA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 223 days.

(21) Appl. No.: 10/002,653

(22) Filed: Oct. 19, 2001

(51) Int. Cl.$^7$ .......................... A61F 2/00; C12N 11/02; C12N 5/06; C12N 5/08
(52) U.S. Cl. .................... 424/423; 424/93.7; 424/426; 435/177; 435/395
(58) Field of Search ............................... 424/423, 426, 424/927; 435/177, 395

(56) References Cited

U.S. PATENT DOCUMENTS

| | | | |
|---|---|---|---|
| 4,060,081 A | 11/1977 | Yannas et al. | 128/156 |
| 4,280,954 A | 7/1981 | Yannas et al. | 260/123.7 |
| 4,505,266 A | 3/1985 | Yannas et al. | 128/1 R |
| 5,460,962 A | 10/1995 | Kemp | 435/238 |
| 5,674,290 A * | 10/1997 | Li | 424/423 |

OTHER PUBLICATIONS

Cheung et al., "The effect of γ-irradiation on collagen molecules, isolated α-chains, and crosslinked native fibers", *J. Biomedical Material Research* 1990 24:581-589.
Hodde et al., "Glycosaminoglycan Content of Small Intestinal Submucosa:A Bioscaffold for Tissue Replacement", *Tissue Engineering* 1996 2 (3) :209-217.
Kato et al., "Regeneration of Achilles Tendon with a Collagen Tendon Prosthesis", *Journal Bone Jt. Surgery* 1991 73:561-574.
Lantz et al., "Small Intestinal Submucosa as a Vascular Graft: A Review", *J. Invest. Surg.* 1993 6:297-310.
Valentino et al., "Radiation and Intra-arterial Cisplatin—Effects on Arteries and Free Tissue Transfer", *Archives of Otolaryngology—Head and Neck Surgery* 2000 126 (2) :215-9.

* cited by examiner

*Primary Examiner*—David M. Naff
(74) *Attorney, Agent, or Firm*—Licata & Tyrrell P.C.

(57) ABSTRACT

Compositions of cross-linked collagen and a glycosaminoglycan are provided which retain characteristics rendering them useful as tissue engineering matrices or scaffolds following terminal sterilization. Also provided are methods for producing these compositions and terminally sterilized matrices or scaffolds from these compositions as well as methods of using these matrices or scaffolds as tissue engineering devices.

2 Claims, 3 Drawing Sheets

COLLAGEN/GLYCOSAMINOGLYCAN MATRIX STABLE TO STERILIZING BY ELECTRON BEAM RADIATION

This invention was supported in part by funds from the U.S. government (NIH Grant No DK56504-01) and the U.S. government may therefore have certain rights in the invention.

FIELD OF THE INVENTION

The present invention relates to compositions comprising collagen and a glycosaminoglycan (GAG) which are useful in terminally sterilized tissue engineering matrices or scaffolds. Collagen/GAG compositions are easily damaged by conventional sterilization techniques. However, matrices or scaffolds comprising the collagen/GAG compositions of the present invention are resistant to damage from terminal sterilization techniques, retaining their function as structural supports, frameworks for tissue formation, cell contact surfaces and therapeutic delivery systems following sterilization via ionizing radiation such as electron beam (E-beam) radiation. Also provided in the present invention are methods for preparing collagen/GAG compositions with increased cross-link densities for use as terminally sterilized matrices or scaffolds as well as methods for using the terminally sterilized matrices or scaffolds. The terminally sterilized collagen/GAG matrices or scaffolds of the present invention are useful as medical applications, particularly in the promotion of dermal regeneration.

BACKGROUND OF THE INVENTION

Collagen is a natural body material useful in a wide range of medical applications. The incorporation of glycosaminoglycans (GAG) into collagen is recognized as providing for a matrix that allows for regeneration of primary tissues. Thus, collagen/GAG matrices represent a particularly useful family of collagen-containing materials.

Collagen/GAG matrices and methods for their production are described in U.S. Pat. No. 4,060,081, U.S. Pat. No. 4,280,954, and U.S. Pat. No. 4,505,266. These biodegradable matrices are useful in a variety of biochemical applications, including, but not limited to dermal replacement constructs. For example, the dermal replacement layer of the INTEGRA® Dermal Regeneration Template™ is comprised of a porous matrix of fibers of cross-linked bovine tendon collagen and the glycosaminoglycan chondroitin-6-sulfate. This commercially available bilayer membrane system for skin replacement is useful in the treatment of deep, partial-thickness, or full-thickness thermal injury to the skin such as third-degree burns. Following application to the wound, the bilayer functions as an artificial skin that provides immediate post-excisional wound homeostasis, facilitating patient recovery and relieving metabolic stress.

However, compositions comprising collagen and GAG are sensitive to the sterilization normally applied to medical products. Thus, presently compositions comprising collagen and GAG which are to be used as matrix materials are commonly immersed in 70 percent isopropyl alcohol (IPA) for packaging and storage. Immersion in IPA does not alter either the cross-link density or other important structural features of collagen-mucopolysaccharide composites which render them useful as matrices or scaffolds.

However, under current Federal and Drug matrix materials cannot be labeled as sterile. As a result, under FDA regulations, collagen/GAG matrix materials cannot be used sub-dermally.

Further, packaging the collagen/GAG matrix materials in IPA is inconvenient for the end user because IPA must be treated as a hazardous chemical waste that must be disposed of properly. In addition the shipping costs for IPA packaged materials are substantially higher.

There is, therefore, a need for methods of sterilizing collagen/GAG compositions to be used as matrix or scaffold materials.

Various attempts to sterilize collagen alone and collagenous tissues have been made.

Physical sterilization methods include heating by boiling, autoclaving and/or microwave. However, heating results in coagulation of collagen containing soft tissues. Further, temperatures above 60° C. to 65° C. result in denaturing of collagen.

Chemical sterilization methods include exposure to agents such as formaldehyde and glutaraldehyde. However, these agents also cross-link collagen, thereby increasing its stiffness, while decreasing its remodeling ability following implantation (Kato et al. Journal Biol. Jt. Surgery 1991 73:561). These chemical sterilization methods also leave residual amounts of the chemicals in the collagen. Accordingly, chemical sterilization methods are not applicable to terminal sterilization since materials with chemical residuals cannot be implanted in the body. Further, chemical sterilants such as ethyl and isopropyl alcohol are not suitable for collagen sterilization as these agents are not sporicidal. The chemical sterilant ethylene oxide is also not suitable for wet aqueous materials as the hydrolysis of ethylene oxide becomes a concern.

U.S. Pat. No. 5,460,962 discloses a method for sterilizing collagen and collagenous tissues with low concentration peracetic acid solutions in either neutral or high ionic strength that prevent or minimize swelling of the collagen or collagenous tissue. However, since matrices with residual periacetic acid cannot be implanted in the body, this method is also not practical for terminal sterilization.

Gamma-irradiation between 0.5 and 2.5 mega-rads has also been used to sterilize tissues. However studies have shown that collagen is damaged by gamma-irradiation at 1 mega-rad (Chueng et al. J. Biomedical Material Research 1990 24:581–590), and at sterilizing doses it is damaged to a degree that compromises the desired function of the present matrices.

Accordingly, attempts to sterilize collagen alone have been relatively unsuccessful. Further such methods for sterilization are oftentimes not applicable to compositions comprising both collagen and GAG. For example, ethylene oxide reacts irreversibly with the free amino groups within the collagen/GAG matrix thereby altering the material chemically.

Sterilization by beta-irradiation has been suggested as a means to avoid decreases in mechanical properties observed following gamma-irradiation of collagen and chondroitin 4-,6-sulphate biomaterials designed for the coverage of serious burns (Berthod et al. Clinical Materials 1994 15(4): 259–65). However, this method cannot be applied to wet collagen/GAG samples of any significant thickness which are often required in medical applications.

Electron beam sterilization processing was developed in 1956 by Johnson and Johnson for sterilization of medical devices. The original systems were inferior compared to gamma irradiation. However, more recent improvements in the reliability and performance of critical accelerator components from industrial involvement in the development of radiographic and oncology machines has resulted in the reevaluation of electron beam technology.

Phase I SBIR Grant [DK56504-01 submitted by Integra LifeSciences Corporation] which was funded on Feb. 19, 2001 suggests use of electron beam (E-beam) irradiation as an alternative to gamma-irradiation to sterilize RGD peptide-containing collagen-GAG matrices for use in islet cell transplantation. High intensity E-beam processing radiation exposure time is less than one minute as compared to 2 to 6 hours with gamma-irradiation. This time decrease is hypothesized to result in less damage from oxidative effects on the products due to the shorter time frame for free radicals to interact with oxygen molecules in and around the product producing ozone and oxidative damage. Increasing the amount of cross-linking is proposed as a possible means for accommodating for minimal degradation expected upon sterilization of the RGD peptide-containing collagen/GAG matrix by E-beam irradiation while retaining the degree of cross-linking required for the maintenance of optimal biological activity.

E-beam irradiation has also been used to sterilize small intestinal submucosa, a resorbable biomaterial containing a high content of glycosaminoglycans that is used in tissue grafts of vascular, urologic, dermatologic, neurologic and orthopedic injury (Hodde et al. Tissue Engineering 1996 2(3):209–217; Lantz et al. J. Invest. Surg. 1993 6:297–310). However, this material is not intended for use in promoting tissue regeneration nor has that use for it been demonstrated.

Studies comparing the physicochemical and biodegradative properties of human amniotic membranes cross-linked via gamma-ray or E-beam radiation or via glutaraldehyde showed a decrease in tensile strength and elongation at break of the amniotic membrane in both the gamma-ray and E-beam irradiated membranes. This decrease in tensile strength and elongation at break of the amniotic membrane are suggested to be caused by scission of collagen chains through irradiation (Valentino et al. Archives of Otolaryngology—Head and Neck Surgery 2000 126(2): 215–9).

Further, as demonstrated herein, E-beam radiation of INTEGRA® Dermal Regeneration Template™ which comprises a collagen/GAG matrix caused both physical and chemical changes in the INTEGRA® Dermal Regeneration Template™. E-beam sterilization experiments in a dry collagen/GAG matrix expected to be less susceptible to radiation damage as compared to wet collagen also revealed changes in the molecular weight and cross-linking density causing biological consequences.

SUMMARY OF THE INVENTION

An object of the present invention is to provide a composition comprising collagen and a glycosaminoglycan which can be used in a terminally sterilized matrix or scaffold. In a preferred embodiment, the composition is produced via a method that has been modified to increase the cross-link density of the collagen and glycosaminoglycan composition.

Another object of the present invention is to provide methods for producing collagen and glycosaminoglycan compositions and matrices or scaffolds comprising these compositions which retain their function as structural supports for cells, frameworks for tissue formation, surfaces for cell contact and therapeutic delivery systems following terminal sterilization of the compositions or matrices or scaffolds comprising these compositions. In these methods, preparation of the collagen and glycosaminoglycan composition is modified to increase the cross-link density of the matrix to an amount that stabilizes the composition toward ionizing radiation while retaining the physical and biological properties necessary to achieve optimal biological performance of the composition as a matrix or scaffold.

Yet another object of the present invention is to provide methods for using these terminally sterilized collagen/glycosaminoglycan matrices or scaffolds as tissue engineering devices. In a preferred embodiment, the terminally sterilized matrices are used as skin substitutes. Moreover, terminal sterilization of these matrices allows for their use in subdermal applications as well.

DETAILED DESCRIPTION OF THE INVENTION

Figure 1:
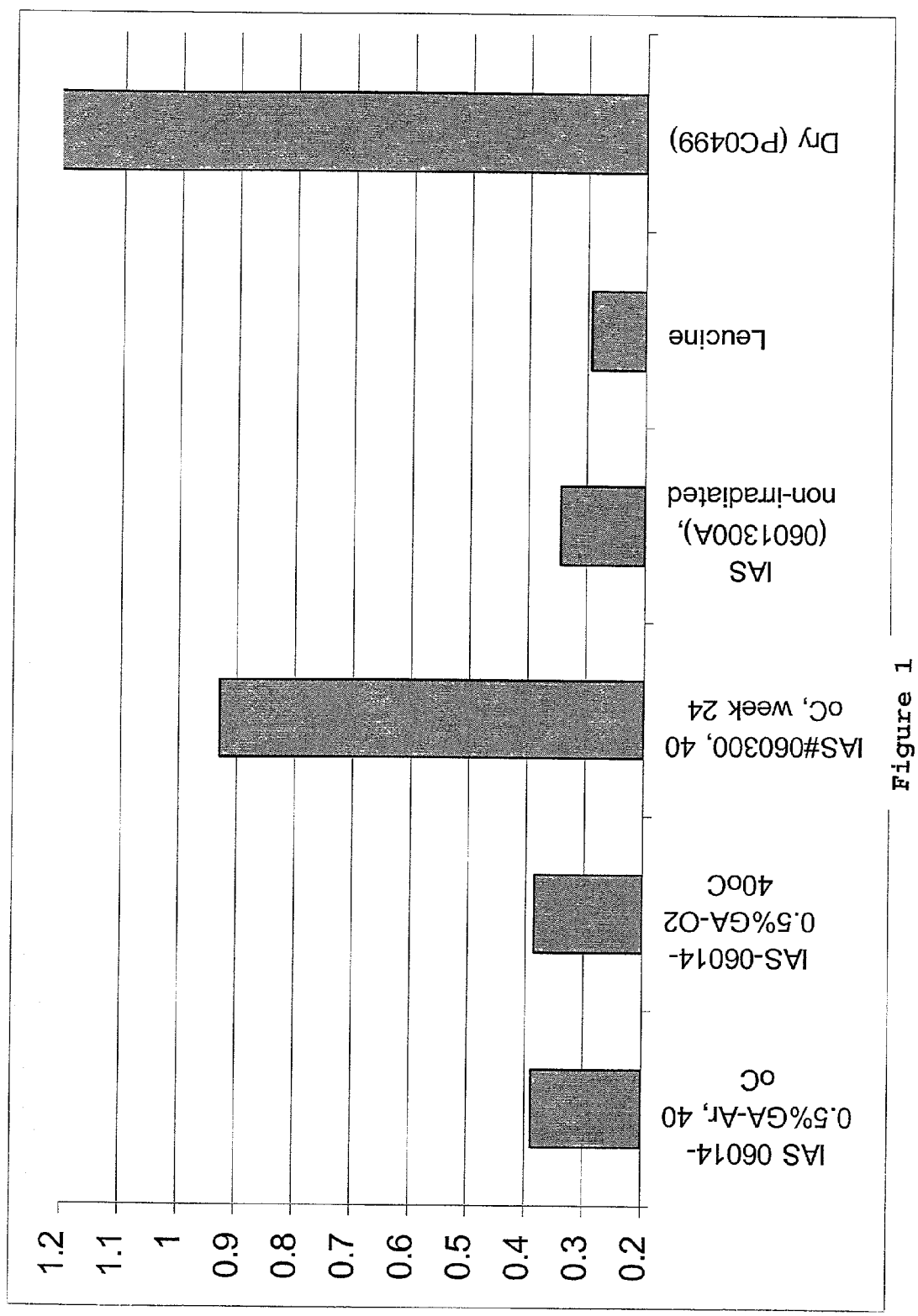
FIG. 1 is a bar graph depicting results from an enzyme degradation study comparing aged collagen/GAG matrices cross-linked under standard conditions and the modified conditions of the present invention.

The present invention provides compositions comprising a collagen and a glycosaminoglycan (GAG) with a modified cross-link density which retain their structure and function following terminal sterilization for use as matrices or scaffolds of tissue engineering devices. Terminally sterilized matrices or scaffolds produced from the collagen/GAG compositions of the present invention are stabilized against degradation caused by sterilization techniques so that they retain their function as tissue regenerative devices upon terminal sterilization via techniques such as ionizing radiation, particularly E-beam irradiation.

As used herein for purposes of the present invention, by "a glycosaminoglycan" it is meant to be inclusive of compositions comprising one or more glycosaminoglycans.

As used herein for purposes of the present invention, the terms "matrix", "matrices", "scaffold" or "scaffolds" refer to a construct of natural or synthetic biomaterials, particularly collagens and their derivatives that can be used in a composite with a glycosaminoglycan (GAG), which are used in vivo and in vitro as structural supports for cells and tissues, frameworks for tissue formation and regeneration, surfaces for cell contact, or delivery systems for therapeutics. Thus, by the term matrix or scaffold, it is meant to include load-bearing materials, bulking agent and fillers, and physiological barriers as well as frameworks for tissue formation and delivery systems for cells, biomolecules, drugs and derivatives thereof.

For purposes of the present invention, by "sterilized" matrix or scaffold it is meant a matrix or scaffold which is treated via a single procedure or a combination of procedures which reduce the number of microorganisms capable of growing in the matrix or scaffold under conditions at which the matrix or scaffold is stored and/or distributed below a level determined by a standardized sterilization protocol and/or validation test such as subsections <1211> and <71> of the U.S. Pharmacopoea.

By the term "terminally sterilized" it is meant a matrix or scaffold sterilized, as defined in the preceding paragraph, in its final packaging for storage and distribution prior to use. In a preferred embodiment of the present invention, the collagen/GAG compositions of the present invention are terminally sterilized via ionizing radiation such as E-beam irradiation.

E-beam irradiation is a preferred sterilization technique for the present invention as compared to gamma and ethylene oxide sterilization because of the short processing time. Electron beam processing has the shortest process cycle of any currently recognized sterilization method. In electron beam processing, products are exposed to radiation for seconds, with the bulk of the processing time consumed in transporting products into and out of the radiation shielding. Overall process time, including transport time, is 5 to 7 minutes. Electron beam processing involves the use of high energy electrons, typically with energies ranging from 3 to 10 million electron volts (MeV), for the radiation of single use disposable medical products. The electrons are generated by accelerators that operate in both a pulse and continuous beam mode. These high energy levels are required to penetrate product that is packaged in its final shipping container. As the beam is scanned through the product, the electrons interact with materials and create secondary energetic species, such as electrons, ion pairs, and free radicals. These secondary energetic species are responsible for the inactivation of the microorganisms as they disrupt the DNA chain of the microorganism, thus rendering the product sterile.

Characteristics of compositions of the present invention which are monitored to insure that a matrix or scaffold comprising the composition retains its functions as a structural support for cells and tissues, a framework for tissue formation and regeneration, a surface for cell contact, or a delivery system for therapeutics upon terminal sterilization include, but are not limited to, porosity, density, degradation resistance or residence time, melting temperatures, water absorption characteristics, surface properties, compressibility, tensile strength, stiffness, cytotoxicity, irritation and sensitization, systemic toxicity, cell adhesion properties, bacterial endotoxin contents and presence of degradation production such as gelatine. Various standard methods for evaluating compositions of the present invention exhibiting one or more of these characteristics upon terminal sterilization have been described. In a preferred embodiment, compositions of the present invention are evaluated for their ability to retain their function as matrices or scaffolds following terminal sterilization in accordance with standards and methods for one or more of these characteristics as set forth by the American Society for Testing and Materials.

Despite suggestions in Phase I SBIR Grant No. DK56504-01 that the shorter time frame of E-beam radiation may provide for less oxidative effects and damage resulting there from on collagen/GAG containing products, it has now been found that current collagen/GAG matrices such as the INTEGRA® Dermal Regeneration Template™ cannot be terminally sterilized via E-beam irradiation without significant damage. Upon E-beam irradiation, significant damage of the matrix occurred after approximately five days. This damage slightly increased over time and caused the product to fail in the collagenase digestion assay, one of the release criteria for INTEGRA® Dermal Regeneration Template™. The damage upon irradiation negatively impacted the performance of the product in in vivo models to such an extent that serious concerns regarding scar formation and loss of the ability for the promotion of tissue regeneration were raised.

The standard method for the production of collagen/GAG matrices is provided in example 1.

It has now been found, however, that modifying the cross-link densities of compositions comprising collagen and GAG significantly alters the stability of the compositions towards E-beam irradiation. For example, it has now been demonstrated that a single additional cross-linking step or a single cross-linking step at a higher concentration of a cross-linking agent such as glutaraldehyde than currently taught enhances the stability of the composition towards E-beam irradiation in such a manner that the characteristics of matrix comprising the composition after E-beam irradiation are comparable to that of a matrix prepared by the standard method (see Example 1) without irradiation. Further, this is achieved without causing a degree of over cross-linking that, in and of itself, compromises the biological performance. Accordingly, the collagen/GAG compositions of the present invention and the modified methods for their preparation are useful in producing matrices or scaffolds which retain functionality following terminal sterilization.

FIG. 1 shows results of the AH-52 collagenase assay that compares, six months after irradiation, a matrix comprising a collagen/GAG composition with increased cross-link density prepared in accordance with the modified method of the present invention with a collagen/GAG matrix prepared in accordance with standard conditions. These results demonstrate the differences between E-beam irradiation (dose:20 kGy) on a lot of regular INTEGRA® Dermal Regeneration Template™ and a matrix comprising a collagen/GAG composition of the present invention cross-linked by using a higher concentration of the cross-linking agent glutaraldehyde. As shown by FIG. 1, the irradiated regular INTEGRA® Dermal Regeneration Template™ fails the release specifications on this assay under these conditions, whereas the matrix prepared via the modified method is equivalent after irradiation to non-irradiated regular INTEGRA® Dermal Regeneration Template™. More specifically, the material labeled "IAS060300 40° C. week 24" was cross-linked under standard conditions (0.25% glutaraldehyde) and irradiated with a dose of 20 kGy. This material would fail the release specification of the current product. The material labeled "IAS 06014-0.5% GA-Ar 40° C." is material that was subjected to higher glutaraldehyde concentration (0.05 M) and irradiated at a dose of 20 kGy. This material, after irradiation, is comparable to the non-irradiated material IAS06013A also shown in FIG. 1. The bars labeled "Leucine" and "dryPC$_{0499}$" are controls for the assay. The leucine control is necessary to assure the quality of the ninhydrin solution used in the assay, the "dry" control is a collagen-GAG matrix that was only subjected to dehydrothermal treatment. Thus, as demonstrated by data in FIG. 1, matrices comprising the collagen/GAG compositions of the present invention are cross-linked to an extent that allows the material to withstand the damage that occurs during the irradiation.

Figure 2:
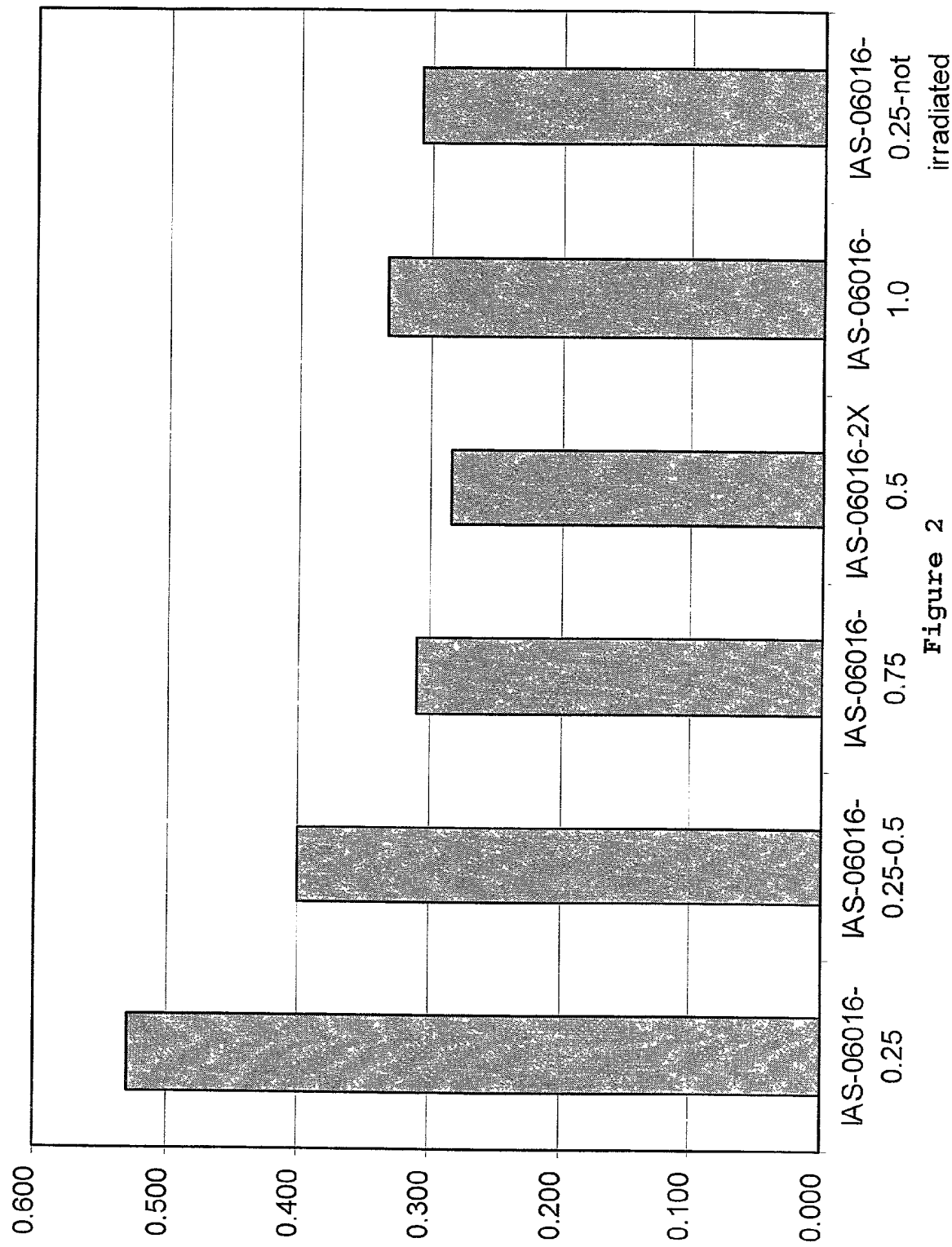
FIG. 2 is a bar graph depicting results from an enzyme degradation study comparing matrices cross-linked at different glutaraldehyde concentrations.
Figure 3:
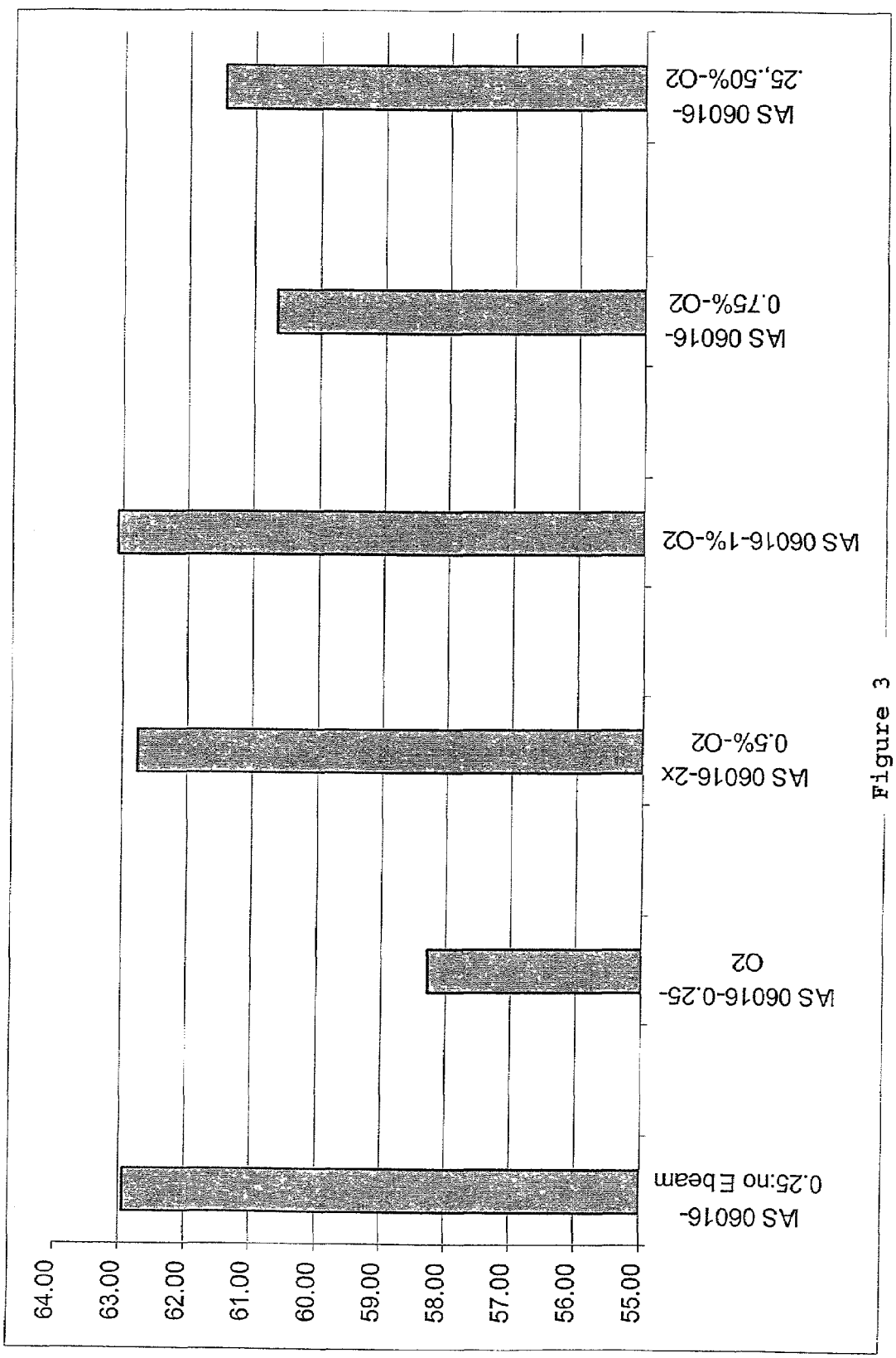
FIG. 3 is a bar graph showing differential scanning calorimetry values of irradiated samples cross-linked at different glutaraldehyde concentrations.

FIG. 2 and FIG. 3 show results from an enzyme degradation assay and Differential Scanning Calorimetry (DSC), respectively, of irradiated collagen/GAG matrices with different cross-linking densities. All matrices were E-beam irradiated at 20 kGy. As shown in FIG. 2, the matrix prepared under standard conditions using 0.25% glutaraldehyde for cross-linking was very close to failing the enzyme degradation assay and, thus, the release specifications immediately after the irradiation. In contrast, matrices comprising collagen/GAG compositions of the present invention prepared with higher concentrations of glutaraldehyde and/or an additional cross-linking step exhibited degradation patterns similar to collagen/GAG matrices prepared by standard conditions and which were not exposed to E-beam radiation. FIG. 2 shows the results of the enzyme degradation assay for irradiated material (from left to right) using standard conditions 0.25% glutaraldehyde, 0.25% followed by 0.5% glutaraldehyde treatment, 0.75% glutaraldehyde treatment, two consecutive 0.5% treatment and a treatment with 1% glutaraldehyde. On the far right, the result for non-irradiated material manufactured using the standard procedures is shown.

The DSC values (depicted in FIG. 3) showed differences as well. In this assay, the temperature of the transition in a collagen material reflects the temperature at which denaturation takes place and this temperature is directly proportional to the level of cross-linkage. The materials that were cross-linked at higher glutaraldehyde concentrations denature at higher temperatures.

While the stable terminally sterilized collagen/GAG matrices used in these experiments were prepared using an increased concentration as compared to standard conditions of the cross-linking agent glutaraldehyde and/or an additional cross-linking step with glutaraldehyde, similar results are expected with other cross-linking methods.

Covalent cross-linking can be achieved by various coupling or cross-linking reagents, some of which are suitable for biological applications.

One suitable chemical method for covalently cross-linking collagen/GAG matrices is known as aldehyde cross-linking. In this process, the materials are contacted with aqueous solutions of aldehyde, which serve to cross-link the materials. Suitable aldehydes include formaldehyde, glutaraldehyde and glyoxal. The preferred aldehyde is glutaraldehyde because it yields a desired level of cross-link density more rapidly than other aldehydes and is also capable of increasing the cross-link density to a relatively high level. When glutaraldehyde is used as the cross-linking agent, it is preferred that nontoxic concentrations of greater than about 0.25% be used. Other chemical techniques that are suitable for increasing cross-link density in the present invention include carbodiimide coupling, azide coupling, and diisocyanate cross-linking.

Any of these cross-linking techniques can be used in the modified methods of the present invention to increase the cross-link density of the matrix and to produce collagen/GAG matrices resistant to damage from terminal sterilization via ionizing radiation.

Collagen derived from any source is suitable for use in the compositions of the present invention, including insoluble collagen, collagen soluble in acid, in neutral or basic aqueous solutions, as well as those collagens that are commercially available. Typical animal sources for collagen include but are not limited to recombinant collagen, fibrillar collagen from bovine, porcine, ovine, cuprine and avian sources as well as soluble collagen from sources such as cattle bones and rat tail tendon.

The term glycosaminoglycan or GAG describes hexosamine-containing polysaccharides. Another name often used for this class of compounds is mucopolysaccharides. Chemically, GAG are alternating copolymers made up of residues of hexosamine glycosidically bound and alternating in a more or less regular manner with either hexuronic acid or hexose moieties. A preferred GAG for use in the present invention is chondroitin 6-sulfate. However, other GAG are suitable for forming the composite materials described herein, and those skilled in the art will either know or be able to ascertain, using no more than routine experimentation, other suitable GAG. For a more detailed description of GAG, see Aspinall, G. O., Polysaccharides, Pergamon Press, Oxford (1970).

Compositions of the present invention may further comprise a silicone layer applied to the collagen and GAG composition prior to cross-linking. This layer is applied in accordance with well known techniques. An exemplary method for application of the silicone layer to a collagen/GAG composition is set forth herein in Example 2.

In a preferred embodiment for preparing the terminally sterilizable collagen/GAG matrices of the present invention, a collagen slurry is first prepared. Various methods for preparing collagen slurries are known. In one embodiment, collagen is prepared by precutting limed calf hides into strips ⅜" wide and then into thin pieces. These thin pieces of hide are contacted with three parts of water containing 0.3% propionic acid and 0.1% benzoic acid Equilibrium is established after four hours at which time the solution had a pH approaching 5.3.

The collagen slurry is then purified. For slurries prepared from calf hide, purification can be achieved by repeated precipitation from a turbid dispersion in 0.05 M acetic acid with 0.2 M sodium dihydrogen diphosphate, $NaH_2PO_4$.

For the preparation of a purified collagen from bovine tendon, the following procedure can be used. Bovine tendon is sliced to a thickness of smaller than about 0.3" and treated with an approximately 0.1% solution of ficin in water at 37° C. while the pH is maintained at around 6.2. The fat on the surface is skimmed off after adequate reaction time and the enzyme is deactivated. This can be done in a number of different ways, such as with a solution of 1% ammonium nitrate solution containing 0.1% sodium chlorite. The enzyme treated tendon slices are ground or homogenized and a 23–25% solution of sodium sulfate containing 6–6.5% sodium hydroxide at approximately 25° C. can be used. After an adequate reaction time the solution is then acidified with an appropriate acid such as dilute sulfuric acid to a pH of about 4.6. The tendon collagen is washed with water until the wash water is clean which in case of sulfuric acid means that it should be sulfate free.

After purification, collagen is dispersed in 0.05 M acetic acid or in a citric acid-buffer solution at pH 3.2 (0.1 M citric acid, 0.2 M sodium dihydrogen diphosphate). The dispersion is thoroughly homogenized in a blender until the absorbance at 440 nm of a 0.3% (W/V) collagen dispersion is about 0.5 as measured on a spectrophotometer. However, as will be obvious to those of skill in the art upon this disclosure other means for purification can be used. The resulting collagen dispersions can be stored at 4° C. until further processing is required.

GAG solutions for use in the matrices of the present invention are preferably prepared from sodium heparin, hyaluronic acid and chondroitin 6-sulfate. In this embodiment, heparin, hyaluronic acid, chondroitin 4-sulfate, heparin sulfate, dermatan sulfate and chondroitin 6-sulfate are dissolved (1% W/V) in a citric acid-phosphate buffer pH 3.2. The GAG solutions are stored at 4° C.

To precipitate collagen-heparin, collagen-chondroitin sulfate and collagen-hyaluronic acid co-precipitates, collagen, preferably 0.1–2% (W/V) dispersed in dilute acid such as 0.05 M acetic acid, is thoroughly agitated at a controlled temperature lower than about 25° C. While the dispersion is mixing, heparin, chondroitin sulfate or hyaluronic acid, preferably at approximately 0.1–15% in dilute acid such as 0.05 M acetic acid, is added drop-wise at a rate of about 0.1 ml per second. The addition of GAG causes collagen to co-precipitate, forming a tangled mass of collagen fibrils coated with GAG. When 90% by weight of collagen is co-precipitated in this manner with 10% by weight GAG, a systematic mass balance shows that about 95% of the added GAG is co-precipitated. After co-precipitation, the tangled mass of fibrils is homogenized in a blender.

To manufacture high porosity matrices comprising collagen/GAG compositions, as are often used in synthetic skin, the composition can be freeze dried. Typical conditions which result in sufficiently high porosity are a temperature of −50° C. and a vacuum of 0.06 mm Hg. However, as will be understood by one of skill in the art upon reading this disclosure, a variety of temperatures or temperature ramping programs can be used depending upon the desired porosity. Further, such variations may involve the use of dehydrothermal treatment to achieve an initial level of cross-linking. In one embodiment, this can be achieved by placing the product in a vacuum oven and exposing the product to a temperature of 115° C. and a vacuum of at least 0.3 mm Hg for 48 hours. At the end of this treatment, less than 10 weight percent of the GAG originally incorporated into the matrix can be removed by 48-hour immersion in a solvent for the GAG.

To manufacture high-density constructs, the collagen/GAG co-precipitates can be filtered and dehydrated to a moisture content of about 20%.

Collagen/GAG compositions prepared as described above can be covalently cross-linked by immersion in a solution of a cross-linking agent such as 0.02–0.2 M solution of glutaraldehyde. This treatment effectively immobilizes a fraction of the GAG component on the collagen fibrils or molecules.

Cross-linking is evidenced by the inability to remove the GAG from the aldehyde-treated composition by prolonged washing with a phosphate buffer solution containing 0.4 M sodium chloride, pH 7.4, a well known solvent for GAGs such as chondroitin 6-sulfate. Alternatively, cross-linking is evidenced by an increased stability against enzyme degradation. Unreacted aldehydes can be removed by treatment with a solution of 5,5-dimethyl-1,3-cyclohexane dione (dimedone) or by implementing an appropriate washing procedure.

As demonstrated herein, the resistance of matrices comprising the collagen-GAG compositions of the present invention to degradation by ionizing radiation, in particular E-beam radiation, is strongly influenced by the number of cross-links per polymer chain. The molecular weight between cross-links ($M_c$) is inversely proportional to the number of cross-links per unit volume. By measuring the stress-strain behavior of thermally denatured collagen-mucopolysaccharide composites, values of $M_c$ can be determined. The technique is described by Treloar, The Physics of Rubber Elasticity, Second Edition, Clarendon Press (1958).

Alternatively, the cross-link density can be monitored by Differential Scanning Calorimetry (DSC) or stability towards enzyme degradation. The higher the number of cross-links in a given material the stronger this material will resist the degradation by enzymes. In the DSC analysis, the transition temperature of a collagen/GAG matrix is measured. This transition reflects the melting of the triple helical structure of collagen and the transition temperature increases with the number of cross-links for a given collagen/GAG composition.

Matrices comprising the collagen-GAG compositions of the present invention prepared via the modified methods of the present invention to increase cross-link density sufficiently so that the matrices retain their function upon terminal sterilization, are then terminally sterilized, preferably via exposure to E-beam radiation at about 15 to about 80 kGy.

After the cross-linking procedure, but prior to sterilization, the matrices are soaked in a suitable buffer, such as 10 mM phosphate buffer. The matrices are then placed in appropriate pouches suitable and compatible with the sterilization procedure. The pouch has to be sealed in such a manner that the seal integrity will not compromise the sterility of the product after sterilization. For certain applications such as the artificial skin wherein the matrix may further comprise a silicon layer in addition to the collagen/GAG composition, it may be preferred to place the matrix on a tray or other suitable device to keep the matrix flat within the pouch, thereby preventing undesirable side effects. In some applications, it is advantageous to submerse the matrix of collagen/GAG composition in buffer solution while in other applications, the fluid contained within the matrix itself is sufficient for storage.

Upon sealing the matrix in the appropriate pouch, the entire pouch is subjected to a sterilization process. In a preferred embodiment, this process comprises subjected the pouch to ionizing radiation, preferably E-beam radiation. The dosage and means by which a product is subjected to the ionizing radiation required for sterilization will vary depending upon a given product and the average bio-burden. However, in a preferred embodiment of the sterilization process, an electron beam with a fixed energy, most commonly 4.5 MeV or 10 MeV, is arranged so that packaged matrices can be moved through the beam on a conveyor belt with a speed that varies based on the desired target dose. The slower the product moves through the beam, the higher the dose that the material is exposed to.

Matrices or scaffolds comprising the collagen/GAG compositions of the present invention produced in accordance with the methods described herein have outstanding properties for many uses.

For example, these matrices and scaffolds are particularly useful in medical and surgical applications, for the regeneration of dermal and sub-dermal tissue. Specifically they can be used for dermal regeneration after excision of burns, scars, and other injuries or for filling of tissue, for example, after excisions of tumors or for cosmetic application such as augmentation of tissue. In this embodiment, the matrix or scaffold is applied to or implanted within a subject at or near the site of the excision or the site where augmentation of tissue is required. Methods for application of such matrices or scaffold are well known by those of skill in the art.

Other applications of terminally sterilizable collagen/GAG matrices of the present invention include, but are not limited to, surgical sutures, blood vessel grafts, catheters and, in general, the fabrication of surgical prostheses. Additionally, these matrices or scaffolds are useful in the fabrication of artificial organs that pump blood, such as artificial kidneys, and blood compatible equipment such as blood oxygenators, as well as in the fabrication of miscellaneous equipment for the handling and storage of blood such as pumps, tubes and storage bags.

The following non-limiting examples are provided to further illustrate the present invention.

EXAMPLES

Example 1

Standard Preparation of Collagen/GAG Matrices

Chondroitin-6-sulfate solution in acetic acid is prepared by mixing 828 grams of deionized water with 2.5 mL of glacial acetic acid and adding to the mixture 2.2 grams of chondroitin-6-sulfate (dry weight). The solution is stirred until the chondroitin-6-sulfate is completely dissolved, preferably for about one hour.

A collagen dispersion of 0.5% collagen in 0.05 M acetic acid is prepared in a mixing vessel with a cooling system cooled to 4° C. Deionized water (4153 grams) is added to the mixing vessel followed by 12.5 mL of acetic acid and the solution is mixed for ten minutes. Purified collagen (25 grams dry weight) is cut into pieces not larger than 1 cm$^2$ and mixed for 5 minutes at 1 to 10° C. at 25 Hz. The emulsifier and disperser is then increased to approximately 50 Hz and run for 30 minutes while maintaining a temperature of <25° C.

While continuing to emulsify and disperse, the chondroitin-6-sulfate solution is then added over a time period of 50 minutes. After the addition is complete, the dispersion is mixed for another hour, while maintaining the temperature at <25° C. After mixing for one hour, the emulsifier and disperser are turned off and the dispersion is degassed under vacuum for 30 minutes.

The dispersion is then poured into trays and lyophilized for 24 hours. After the lyophilization is completed, the trays are placed in a vacuum oven and subjected to dehydrothermal treatment at 105° C. for 16 hours under vacuum. After the dehydrothermal treatment, the collagen/GAG matrices can either be directly cross-linked or subjected to other modification, such as silicone coating and then cross-linked.

The standard cross-linking procedure is carried out in a solution of 0.25% glutaraldehyde in 0.3% acetic acid. During the procedure, the collagen/GAG matrix can be fixed in a suitable frame that holds the matrix in place in the cross-linking solution or, in a lab scale, the cross-linking can be done with the matrix floating in the cross-linking solution. The cross-linking solution is prepared by adding the glutaraldehyde to 0.3% acetic acid solution in deionized water. The solution is allowed to stand for at least 30 minutes before adding the matrices. The matrices are kept in the solution for 20 to 24 hours. The glutaraldehyde solution is then removed and the matrices are washed three times with deionized water and allowed to soak in the deionized water for 1 to 2 hours each wash. Finally, the matrices are subjected to a final soak in deionized water for 16 hours. Afterwards, the matrices are cut to size if necessary and then placed in a foil pouch containing 100 to 120 mL of 70% IPA and sealed. The matrices are refrigerated until use.

Example 2

Application of Silicone Layer

For collagen/GAG construct to be used for dermal regeneration, a thin layer of silicone is applied to the matrices after dehydrothermal treatment and prior to cross-linking. For this purpose, the Gardener knife is used to apply an even layer of silicone. A Gardener knife is set to an appropriate thickness of about 10 mil and two sheets of polyethylene sheeting is cut to a size approximately 6 inches longer than the matrices. A bead of silicone is placed on one of the polyethylene sheets in between the edges of the small Gardener Knife. The Gardener knife is then drawn slowly to the opposite end of the polyethylene sheet. A collagen/GAG matrix is placed onto the silicone and the other sheet of polyethylene is put on top of the collagen/GAG matrix. A second Gardener knife, set to about 50 mil is drawn over the length of the polyethylene-sponge-polyethylene sandwich. The upper sheet of the polyethylene sheeting is removed and the collagen/GAG-silicone bilayer is exposed to air for 1 to 5 hours. Cross-linking, washing and packaging are then carried out as described for the uncoated matrices.

Example 3

Modified Method for Production for Collagen/GAG Matrices of Present Invention Collagen/GAG matrices cross-linked sufficiently to compensate for irradiation damage after E-beam sterilization were produced. In this procedure, the collagen/GAG matrices were cross-linked using a 0.5% glutaraldehyde solution in 0.3% acetic acid. The collagen/GAG matrices were first placed between polyethylene sheets and meshes of an appropriate mesh size. The matrices were held in place by a polypropylene frame. For cross-linking, the polyethylene sheeting was placed into the lower part of the cross-link frame. The matrices were then placed onto the polyethylene sheeting and covered with the mesh. The top part of the frame was placed over the mesh and sheet and the frame was closed. The matrices in the frames were then placed into cross-link racks to air dry for 1 to 5 hours.

A 0.3% acetic acid solution in deionized water was prepared in a tub sufficiently large to hold 2 liters of solution per matrix and the dry matrices were soaked in that solution for 1 to 22 hours. Following this soaking, the 0.3% acetic acid solution was drained and the rack containing the matrices was removed from the tub. A cross-linking solution of 0.5% glutaraldehyde in 0.3% acetic acid was prepared, the rack containing the matrices was placed into a tub containing this solution, and the matrices were left in the cross-linking solution for 22 hours. The glutaraldehyde solution was then pumped into a waste drum, the matrices were washed by filling the tub with deionized water, and the matrices were allowed to sit in the deionized water for 1 to 2 hours. This washing process was repeated twice followed by a final rinse for 12 to 16 hours. Following this rinse, the matrices were placed in a tub containing a 10 mM phosphate buffer, or other appropriate, at pH 6.5, for 1 to 2 hours. The collagen/GAG matrices were then removed from the buffer and cut into appropriate sizes if necessary. The collagen/GAG matrices were then packaged in 10 mM buffer, pH 6.5 using a heat sealer.

Example 4

Enzyme Degradation Assay

The matrix was opened, removed from its package, and laid out on a flat surface. Fifteen 8 mm punches were taken and placed into 10 ml of water in a dish on a shaker which was agitated for 30 minutes. The water was removed and the washing procedure was repeated. Following the washing process, the matrices were placed in 10 ml of Tricine buffer. The punches were then gently blotted and transferred into a 12×75 glass assay tube, 5 punches per tube. An enzyme control which serves as a reagent blank for the test samples and is comprised of only 1.25 ml of the enzyme solution was also prepared.

Collagenase (4 mg; Sigma C-9891) was weighed out and placed into a 50 ml conical tube. Tricine buffer (25 ml) was added and the number of units/ml in the solution was calculated using the specific activity for the dry solid. Thermolysin (4 to 6 mg; Sigma P-1512) was weighed out and suspended at 0.5 mg/ml. The specific activity per ml was calculated as for the collagenase solution.

Using Tricine buffer as a diluent, a final concentration of 0.2 units/ml for collagenase and 0.45 units/ml for thermolysin was established. The sample was then thoroughly mixed without aerating.

Enzyme solution (1.25 ml) was transferred into each tube with a repeating dispenser. The tubes were capped tightly and incubated at 37° C. for 6 hours in a water bath. After incubation the samples were placed on ice and the solution was filtered into a 1.5 mL microcentrifuge tube using a 0.45 $\mu$m filter.

A ninhydrin reagent was prepared fresh for use in the assay. This reagent was prepared by weighing ninhydrin (200 mg) and hydrindantin (30 mg) into a glass test tube and adding 7.5 ml of ethylene glycol monomethyl ether to the tube followed by 5 ml of sodium acetate buffer. A 0.25 ml aliquot of the freshly prepared ninhydrin reagent was then added to 50 $\mu$l of sample in a 12×75 test tube. Three tubes containing 50 $\mu$l of water were included to serve as ninhydrin blank controls. Three tubes containing 50 $\mu$l of a stock 0.10 mg/ml solution of leucine were also included as positive controls.

A dehydrothermal treated matrix that underwent the enzyme treatment was also included as an additional control. For this matrix, 25 $\mu$l of the solution was mixed with 25 $\mu$l of water.

The tubes were heated at 100° C. for 25 minutes. Following heating, the tubes were allowed to cool for about 10 minutes and 2.5 ml of 50% n-propyl alcohol was added to each tube. The tubes were then vortexed and allowed to stand for 15 minutes prior to reading.

The samples were read in a spectrophotometer set at 570 nm and zeroed with the ninhydrin reagent blanks. The order of reading was preferable enzyme blank, IAS control, leucine control, test samples and finally the dry control.

Example 5

Differential Scanning Calorimetry

Differential Scanning Calorimetry determines the temperature and heat flow associated with material transitions as a function of time and temperature. It also provides quantitative and qualitative data on endothermic (heat absorption) and exothermic (heat evolution) processes of materials during physical transitions that are caused by phase changes, melting, oxidation, and other heat related changes.

At a temperature characteristic of the specific sample of collagen, the collagen undergoes an endothermic transition that represents the melting of the triple helical structure of the collagen.

The cross-linking density has a dramatic effect on the observed transition temperature. Samples of non-cross-linked collage/GAG matrices have a transition temperature of approximately 44 to 48° C. After cross-linking the transition temperature increases to 58 to 72° C. depending on the type of cross-linking reagent, concentration and duration of cross-linking.

The prepare samples for this assay, 8±4 mg of damp collagen matrix without silicone backing was loaded into a sealed hermetic pan. When appropriate, punches, usually 4 to 8 mm in diameter were taken from the collagen/GAG matrix.

The wet samples were blotted to dampness. The matrix was loaded into the tared pan, usually in the lid. The weight of the sample was then determined and recorded. The pan was then numbered on the bottom, sealed and loaded, top down, into the autosampler.

The following heating regime was used in the modulated DSC analysis:
Starting Temperature 30° C.
Ramp Rate 3° C./minute
Period 40 seconds
Amplitude 0.318° C.
Ending Temperature 90° C.

Analysis was performed using the TA Universal Analysis software package. This software package calculated the temperature at the energy flow minimum (endothermic up) as well as the onset point temperature at which the transition begins.

What is claimed is:

1. A scaffold or matrix comprising a lyophilized collagen and glycosaminoglycan co-precipitate and a silicone layer applied to the lyophilized collagen and glycosaminoglycan co-precipitate, said lyophilized collagen and glycosaminoglycan co-precipitate cross-linked after application of the silicone layer with glutaraldehyde at a density of cross-linkage and under conditions which stabilize the scaffold or matrix toward electron beam radiation at about 15 to about 80 kGy so that the matrix or scaffold retains characteristics to function as a structural support for cell and tissue ingrowth.

2. A method for producing the scaffold or matrix of claim 1 comprising:
   (a) adding glycosaminoglycan to a collagen solution to co-precipitate collagen fibrils coated with glycosaminoglycan from the solution;
   (b) lyophilizing the collagen and glycosaminoglycan co-precipitate of step (a);
   (c) applying a silicone layer to the lyophilized co-precipitate of step (b); and
   (d) cross-linking the lyophilized collagen and glycosaminoglycan co-precipitate with glutaraldehyde at a density of cross-linkage and under conditions which stabilize the scaffold or matrix toward electron beam radiation at about 15 to about 80 kGy so that the matrix or scaffold retains characteristics to function as a structural support for cell and tissue ingrowth following sterilization.

* * * * *